United States Patent [19]
Willey et al.

[11] Patent Number: 5,432,060
[45] Date of Patent: Jul. 11, 1995

[54] IMMORTALIZED HUMAN BRONCHIAL EPITHELIAL CELL LINE

[75] Inventors: James C. Willey; Curtis C. Harris, both of Bethesda, Md.

[73] Assignee: The United States of America, as represented by the Secretary of the Department of Health and Human Services, Washington, D.C.

[21] Appl. No.: 840,625

[22] Filed: Feb. 21, 1992

Related U.S. Application Data

[63] Continuation of Ser. No. 487,626, Mar. 2, 1990, abandoned.

[51] Int. Cl.$^6$ ............... C12Q 1/02; C12N 5/08
[52] U.S. Cl. ................... 435/29; 435/240.2
[58] Field of Search .............. 435/240.2, 29

[56] References Cited

U.S. PATENT DOCUMENTS 4,885,238  12/1989  Reddel et al. ............... 435/240.2

OTHER PUBLICATIONS

Woodworth, et al. Characterization of Normal Human Exocervical Epithelial Cells Immortalized in vitro by Papilloma . . . Cancer Research vol. 48 pp. 4620–4628 1988.
Pecoraro, et al. Differential Effects of Human Papilloma Virus Type 6, 16, and 18 DNAs on Immortalization and Transformation . . . Proc. Natl. Acad. Sci. (USA) vol. 86 pp. 563–567 Jan., 1989.
Band, et al. Human Papilloma virus DNAs Immortalize Normal Human Mammary Epithelial Cells and Reduce Their Growth Factor Requirements Proc. Natl. Acad. Sci. (USA) vol. 87 pp. 463–467 Jan., 1990.
Ostrow, et al. A Survey of Human Cancers For Human Papillomavirus DNA by Filter Hybridization Cancer (USA) vol. 59 No. 3 pp. 429–434 (Abstract) 1987.
Willey, et al.; Cancer Research, vol. 51, pp. 5370–5377; Oct. 1, 1991.
Syrjänien, et al.; The Lancet; Issue of Jan. 17, 1987; pp. 168–169.
Pecoraro et al, PNAS, USA. 86:563–567, 1989.
Woodworth et al, Cancer Res. 48:4620–4628, 1988.
Band, et al, PNAS, USA. 87:463–467, 1990.
Stoner et al, Abstract, Proc. AACR, 30:218, 1989.
Lechner, et al., "In Vitro Human Bronchial Epithelial Model Systems for Carcinogenesis Studies", In Vitro Models for Cancer Research, vol. VI, Chapter 1, 1983, pp. 3–17.
Pirisi, et al., "Continuous Cell Lines with Altered Growth and Differentiation Properties Originate After Transfection of Human Keratinocytes with Human Papillomavirus type 16 DNA", Carcinogenesis, vol. 9, No. 9 1988, pp. 1573–1579.

*Primary Examiner*—George C. Elliott
*Attorney, Agent, or Firm*—Townsend and Townsend Khourie and Crew

[57] ABSTRACT

Human bronchial epithelial cell lines permanently transformed by human papilloma viruses have been obtained. These cell lines are useful for the study of growth and differentiation in bronchial carcinoma and the identification of chemical and biological agents that may be useful in the therapy of human lung cancer.

8 Claims, 7 Drawing Sheets

IMMORTALIZED HUMAN BRONCHIAL EPITHELIAL CELL LINE

This is a Continuation of application Ser. No. 07/487,626, filed Mar. 2, 1990, now abandoned.

The present invention is related generally to continuously growing human cell lines. More particularly, the present invention is related to a continuously growing human bronchial epithelial cell line permanently transformed by human papilloma virus.

Human bronchial epithelial cells have been immortalized by transformation with SV40 virus (Stoner et al, 1989, *Proc. Amer. Assoc. Cancer Res.*, 30:218). However SV40 is not known to be associated with any human malignancies. In contrast, human papilloma viruses (HPV) are known to be associated with a number of human malignancies including bronchogenic carcinoma, anogenital and esophageal melanoma. A continuously growing human bronchial epithelial cell line permanently transformed with HPV has not heretofore been known or described.

SUMMARY OF THE INVENTION

It is, therefore, an object of the present invention to provide an HPV transformed normal human bronchial epithelial (NHBE) cell line capable of incessant proliferation in suitable culture medium in vitro.

It is a further object of the present invention to provide an immortalized human bronchial epithelial cell line containing actively expressing HPV genes.

It is another object of the present invention to determine the factors and parameters controlling the growth and differentiation of neoplastic human bronchial epithelial cells mediated by HPV.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
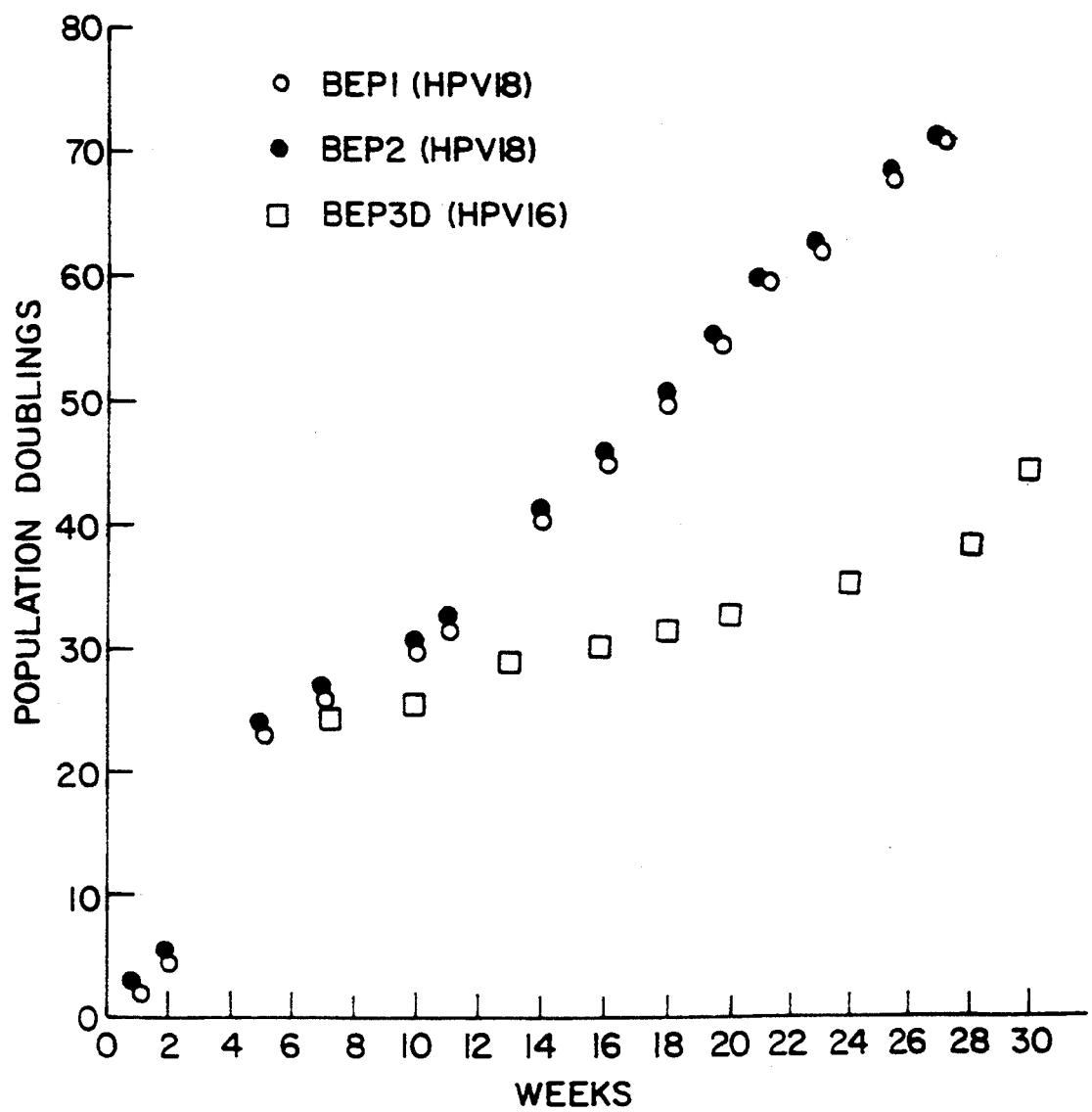
FIG. 1 demonstrates the growth pattern of HPV-transformed human bronchial epithelial cell lines following lipofection at time 0, the number of population doublings was evaluated at each transfer 0, BEP1; , BEP2; ☐, BEP3.
Figure 2A:
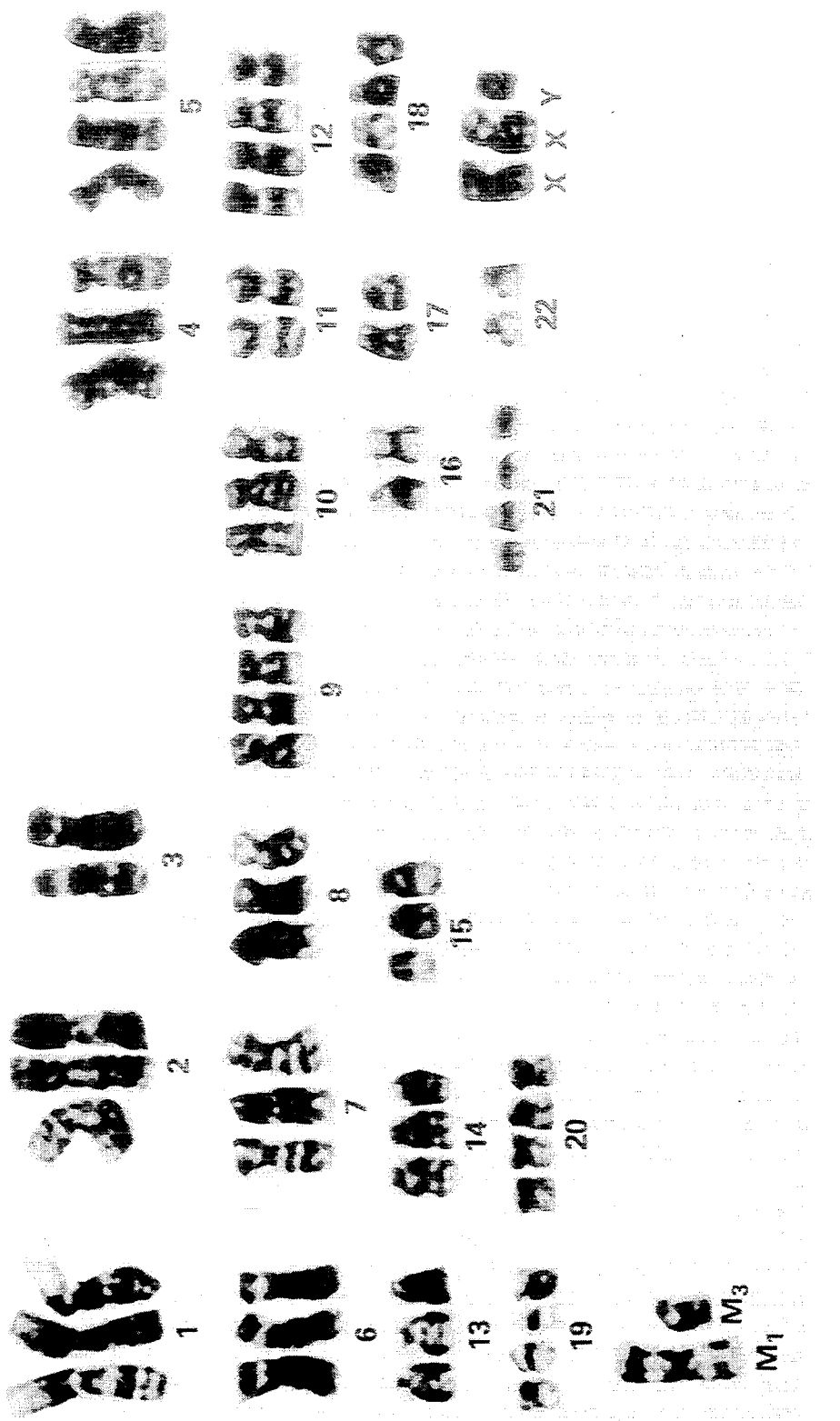
FIGS. 2A, 2B, and 2C shows karyotype analysis.
A. BEP1 cell line, p8.
B. BEP2 cell line, p6.
C. BEP2 cell line, p8 tetraploid
Figure 2B:
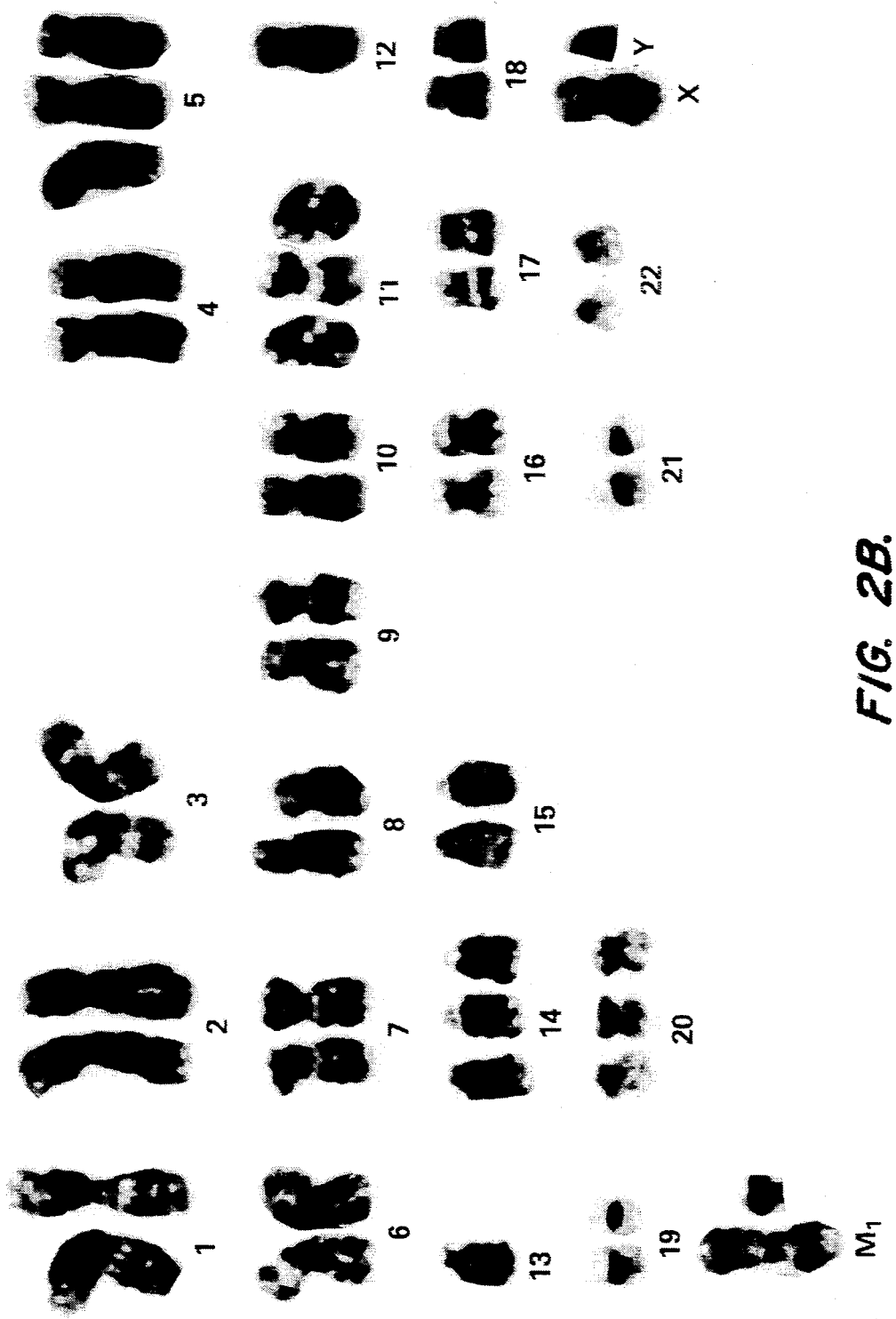
Figure 2C:
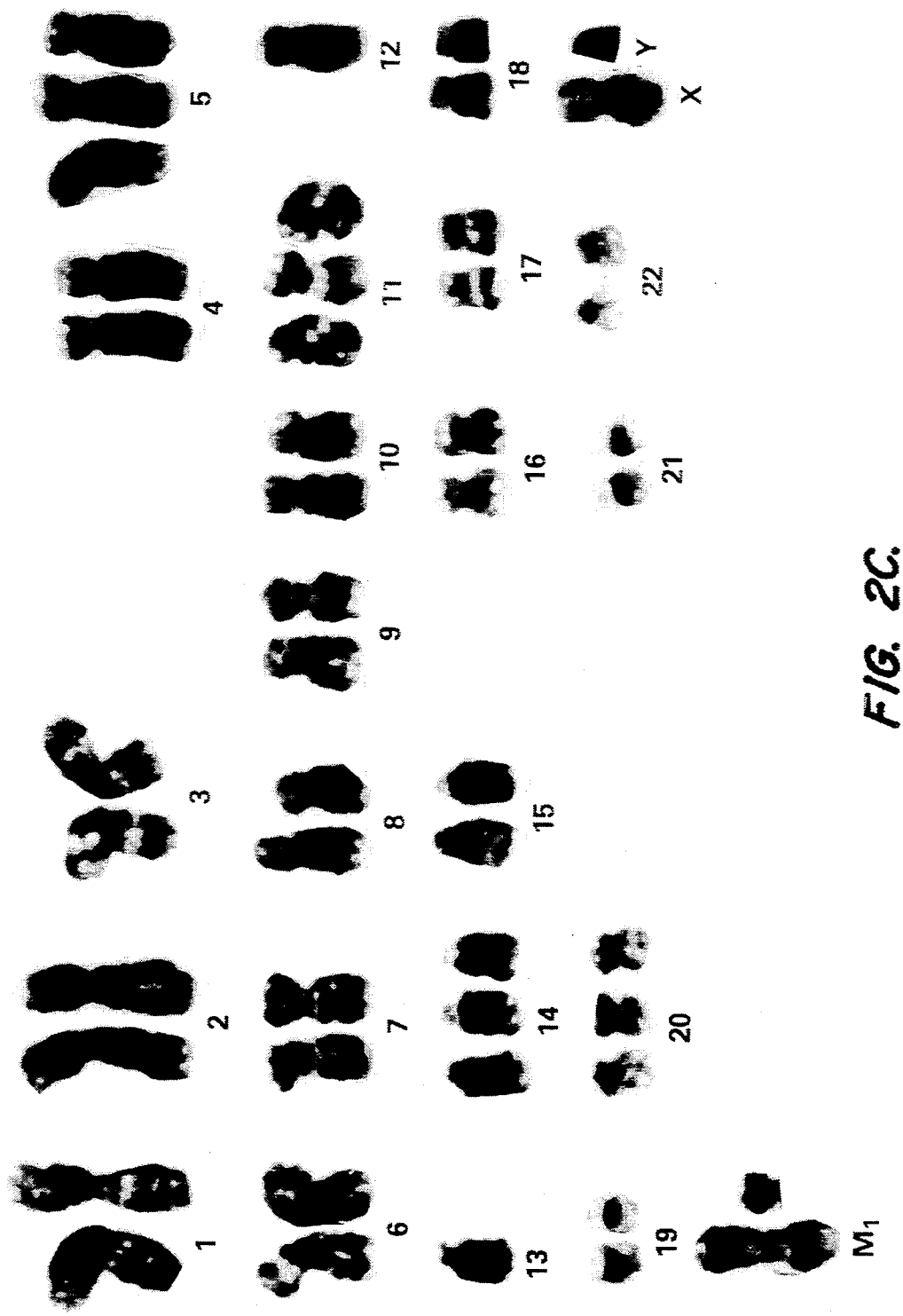
Figure 3:
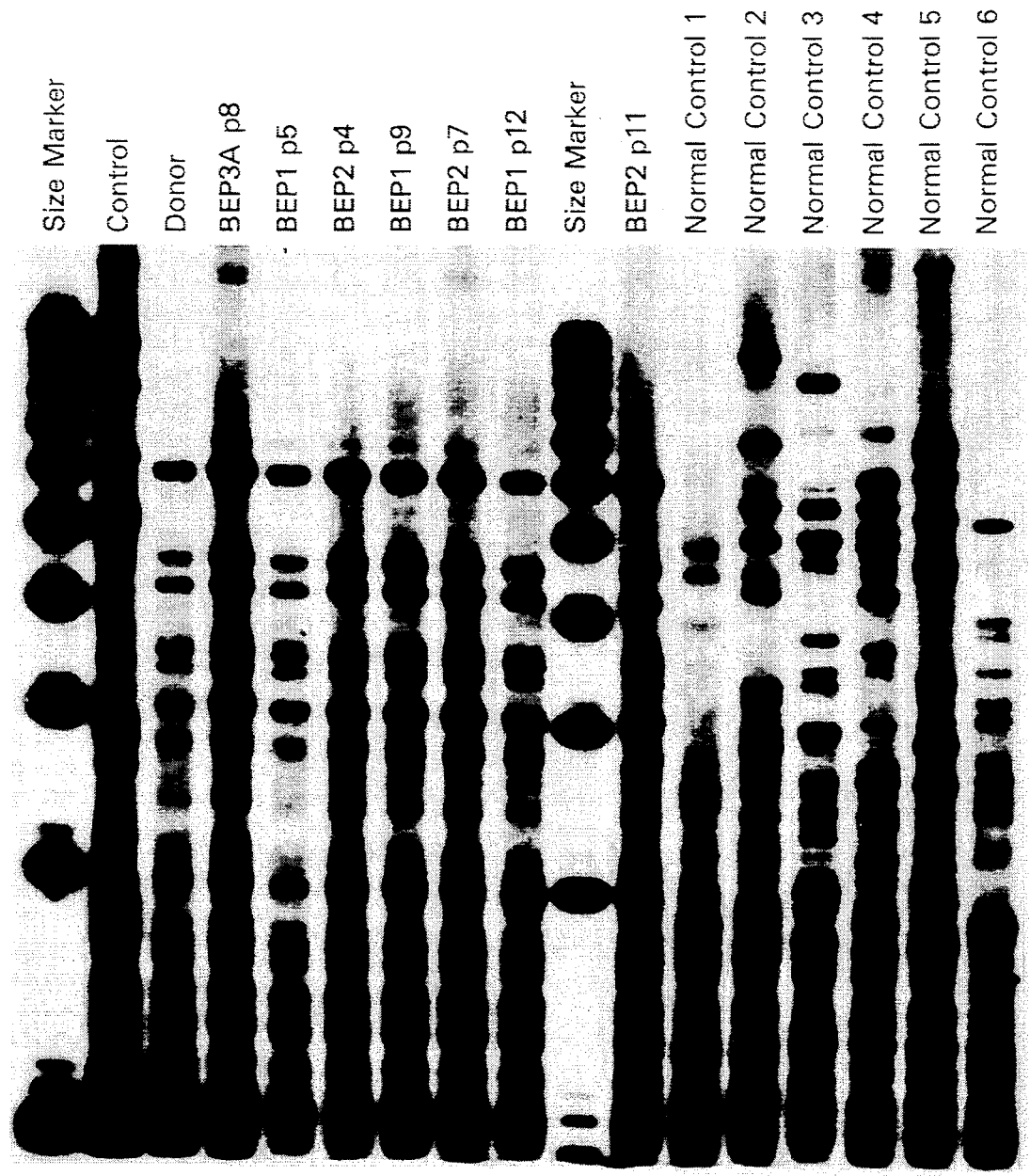
FIG. 3 shows the DNA fingerprint analysis of HPV18 (BEP1,2) or HPV16 (BEP3A) transformed bronchial epithelial cell lines using multilocus probe 33.15.
Figure 4:
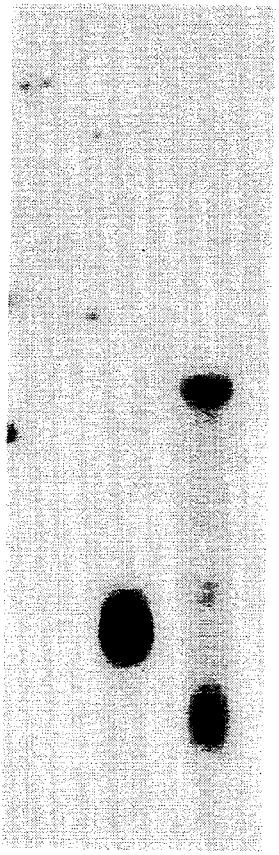
FIG. 4 shows the Northern analysis of HPV18-transformed bronchial epithelial cell lines, normal human fibroblasts, or BEP1 and BEP2 using E6/E7 as probe.
Figure 5A:
FIGS. 5A–5D are photomicrographs of the transformed cell lines.
A. Early passage BEP2.
B. Late passage BEP2.
C. Early passage BEP3.
D. Late passage BEP3.
Figure 5B:
Figure 5C:
Figure 5D:
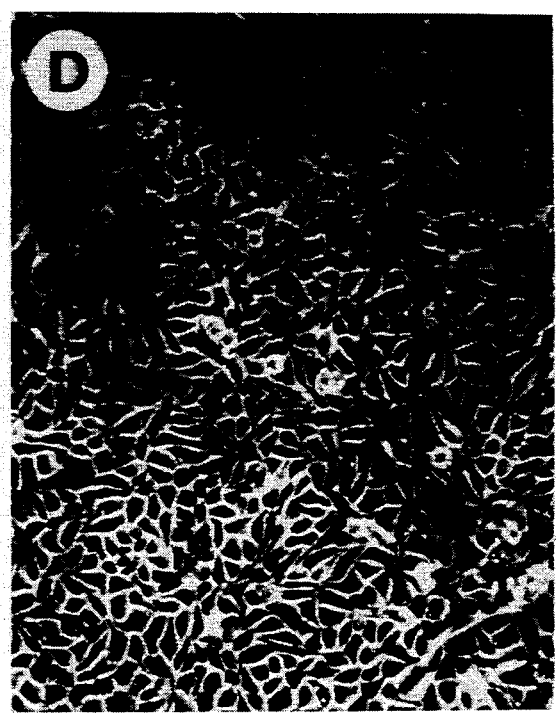

The above and various other objects and advantages of the present invention are achieved by an immortalized human bronchial epithelial cell line transformed by human papilloma virus.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

Various materials were obtained from the sources indicated below. Flasks (Costar), media, buffers, trypsin, bovine fetal calf serum (Biofluids, Rockville, Md.), fibronectin (Collaborative research, Waltham, Mass., and Boeheringer-Mannheim, Indianapolis, Ind.), bovine serum albumin (Miles Scientific, Naperville, Ill.), type I collagen (Vitrogen, Palo Alto, Calif.), agarose (Beckman LE; Beckman LMP, Palo Alto, Calif.), restriction enzymes (New England Biolabs, Beverly, Mass.,). Lipofectin (BRL-Life Technologies, Inc. Gaithersburg, Md.), guinea pig anti-Keratin antiserum, rabbit anti-guinea pig antiserum, phenol (Meloy Laboratories, Inc.. Spring Field, Va.), Nytran transfer membranes (Schleicher and Schuell, Keene. N.H.). molecular markers (BRL-Life Technologies, Inc. Gaithersburg, Md.).

The methodologies are now described.

Normal human bronchial epithelial (NHBE) cells were cultured according to the method of Lechner et al, 1988, *Cancer Res.* 4:3–17. Briefly, one hundred mm culture dishes, coated with a mixture of fibronectin/bovine serum albumin/nitrogen were inoculated with 10 E6 cells, and the cells were incubated in LHC-8 medium. The next day, the medium was removed and replaced with medium containing lipofectin and cloned HPV DNA. The lipofectin and cloned HPV DNA had been each taken up in 4 ml of LHC-8 medium, then mixed together, before the mixture was added to the cells. After 12 h of incubation, the medium was removed and replaced with fresh medium. In the third passage, most of the cells terminally differentiated while 40–50 colonies grew out, and remained in continuous culture. In the control cultures, all of the cells differentiated after the third passage and sloughed off of the flasks.

Lipofection procedure 1. 100 µl of lipofectin placed in polystyrene tubes 1–6 (see below).
2. 4 ml of LHC-8 added
3. 50 µg (20 µg for HPV16) of DNA added to a second tube containing 4 ml LHC-8
4. Tubes mixed and added to dishes of cells.

| Treatment | |
|---|---|
| Tube 1. | No DNA |

-continued

| | Treatment | |
|---|---|---|
| 2. | pBR322 | 50 μg DNA |
| 3. | HPV16 | 20 μg DNA |
| 4. | HPV16 | 50 μg DNA |
| 5. | HPV18 | 50 μg DNA |
| 6. | HPV18 | 50 μg DNA |

At the end of the treatment, the medium with lipofectin was removed, cells were rinsed once with Hepe's buffered salt solution (HBSS), and the cells were incubated in LHC-8 at 37° C. in 3.5% $CO_2$. Routinely, cells are dissociated for passage by washing twice with HBSS to remove debris and calcium, then incubating with 0.05% trypsin, 0.2% EGTA, 0.1 mg/ml bovine serum albumin (BSA) in HBSS for 10 min at 37° C. The cells are collected in medium and pelleted by centrifugation at 1200 rpm in a refrigerated centrifuge for 5 minutes at 4° C. The cells are taken up in 10 ml of LHC medium, counted by placing 15 μl on a hemocytometer, and pelleted a second time. The cells are then either replated for the next passage, frozen viably and stored in liquid nitrogen, or processed for DNA, RNA or for other purposes. During the third passage, cell division appeared to slow and different media were tested for improved cell growth. Costar flasks are used for routine culture. For early passages, cells were passed 1:2. With increased robustness in later passages, cells were then routinely passed 1:10.

Analysis for Keratin

HPV-16 transfected cells from the seventh passage were analyzed for keratin content by incubating on a glass slide with guinea-pig anti-keratin antiserum, followed by incubation with fluorescein labeled rabbit anti-guinea pig anti-serum, then evaluated by fluorescence microscopy using the number 2 fluorescein filter.

Cell Freezing

Pelleted cells were taken up in sufficient volume of freezing medium A to result in a concentration of 2 million cells/ml. An equal volume of freezing medium B was then added and mixed. Two ml of cell suspension was added to each freezing tube. Tubes were placed in a freezing can which was placed in −70° C. freezer overnight. The tubes were transferred from freezing can to liquid nitrogen freezer the next day. When needed, vials were thawed, plated and the viability determined.

Colony Isolation Procedure

Flasks containing colonies were rinsed twice with HBSS. Colonies were rinsed twice and ringed with stopcock grease which had been autoclaved. PET 0.05% was added (enough to cover the colony) and the flask was incubated at 37° C. until cells were dissociated. Dissociated cells were counted, pelleted and transferred to coated T25 flasks in 5 ml LHC-8 medium.

Southern analysis

DNA was obtained from cell lines by standard phenol extraction procedure or by cesium gradient centrifugation.

Phenol extraction

Flasks of cells are washed with HBSS buffer, then 2.5 ml/100 cm2 of lysing solution (1% sodium dodecyl sulfate/150 mM NaCl/10 mM EDTA/10 mM Tris, pH 7.4) is added. After all cells are solubilized, they are transferred to a 50 ml conical tube and proteinase K to a final concentration of 100 μg/ml is added. The lysate is incubated at 65° C. for 10 minutes to inactivate DNAse enzymes, then incubated overnight at 37° C. To this lysate, an equal volume of fresh phenol that has been equilibrated in 50 mM Tris, pH 8.0 is added, and the tube is gently inverted for 5 minutes at room temperature (about 22°–24° C.) then centrifuged at 2000 g for 5 minutes, and the top (aqueous) layer is transferred to a second tube. An equal volume of 50% phenol/50% chloroform (v/v) is then added, and the inversion centrifugation process repeated. The supernatant is then transferred to a third tube, and an equal volume of chloroform is added. After a third inversion, centrifugation cycle, the supernatant is transferred to a fourth tube and the DNA precipitated by the addition of 1/10 volume of 3M NaAcetate, 2.5 vol of cold ethanol. After washing the resulting precipitate with 70% ethanol, and air-drying the pellet, it is re-suspended in TE buffer (10 mM Tris pH 7.4/1 mM EDTA) and RNase to a final concentration of 50 μg/ml is added (The RNase is prepared to be DNase-free by heating the freshly suspended enzyme at 70° C. for 30 minutes. The solution is then extracted with an equal volume of 1:1 SS-phenol:chloroform. The phases are separated by centrifugation, as above, and the supernatant extracted with an equal volume of chloroform. Following centrifugation, the DNA in the supernatant is precipitated with 12.5 ml of ethanol, then washed with 70% ethanol and air-dried. The pellet is then suspended in TE buffer, and the DNA yield determined by O.D. reading at 260 nM and the purity determined by 260/280 ratio. The DNA preparation is stored in TE at 4° C.

Cesium chloride preparation of RNA and DNA from cultured cells

Flasks of cells were washed with HBS then 2.5 ml/100 cm2 of guanidine isothyocyanate (GIT) buffer was added. The guanidine isothyocyanate buffer was 4M GIT / 25 mM sodium acetate, pH6/0.8% beta-mercaptoethanol (v/v). After 3–5 minutes, with gentle rocking, the cell lysates were layered on top of 4 ml of cesium chloride buffer in Beckman SW41 10 ml ultracentrifuge tubes. The tubes were filled to nearly the top with GIT buffer, then they were spun overnight at 32,000 rpm (174,000×g) at 20° C. The GIT solution in the upper two-thirds of the tube was then removed and discarded, the CsCl solution in the lower one third of the tube that contains the DNA was transferred to a second tube. The RNA pellet in the bottom of the tube was re-suspended in 200 μl of 0.3M sodium acetate, pH 6 and transferred to a 1.5 ml microfuge tube. To this tube was added 750 μl of ethanol, and the tube was placed on dry ice for 10 minutes. After microcentrifugation for 10 min., the supernatant was 14 discarded, 300 μl of 70% ethanol was added, and the tube was microfuged again. The supernatant was discarded, and the pellet was dried in a vacuum centrifuge. The pellet was resuspended in 200 μl of dH20. The RNA preparation was stored as an ethanol precipitate at −70° C. The 4 ml of CsCl containing the DNA was diluted with $dH_2O$. To this was added 30 ml of cold ethanol. The DNA precipitate was recovered, transferred to a new 50 ml tube, and rinsed with 70% ethanol, then air-dried. The pellet was then re-suspended in PK buffer, and 10 mg of proteinase K was added. After incubation at 65° C. for 15 minutes, the solution was incubated overnight at 37° C. The hydrolysate was then extracted with 1:1 SS-phenol:chloroform, followed by chloroform, ethanol precipitation, and quantitated as described above.

Restriction digestion, electrophoresis, and Southern transfer

Restriction endonuclease digest conditions were according to the recommendations of the suppliers. For genomic DNA, the restriction digestion was for 4–6 hrs at 37° C. For simple DNA preparations (cloned or PCR amplified) the incubation was for 1–2 hours at 37° C. Generally, 10 μg of DNA was digested in a volume of 150 μl. The digest was precipitated by addition of 3 μl 5M NaCl and 375 μl (2.5 vol) of cold ethanol, microfuged for 10 minutes at 4° C., washed with 500 μl cold 70% ethanol and microfuged.

The pellet was air-dried in a vacuum microfuge and resuspended in 17 μl of electrophoresis running buffer (routinely TAE buffer) and 3 μl of gel loading buffer (TAE buffer containing 504 glycerol/1% saturated bromphenol blue), heated to 68° C. for 10 minutes, and loaded into wells of an agarose gel, along with a lambda-HindIII digest in a separate well to serve as a size marker. The concentration of agarose in the gel was 1.04. Following electrophoresis for 8–16 hours, the gel was stained with ethidium bromide, the migration distance of the marker bands measured and recorded, and the gel photographed.

The digested DNA was vacuum-transferred to a Nytran membrane. The gel was laid on top of the Nytran membrane on the vacuum apparatus, covered with 500 ml of 0.4M NaOH/0.8M NaCl and a vacuum pressure of 50 cm of water applied for four minutes. The NaCl-NaOH solution was removed, 500 ml of 10×SSC added, and a pressure of 50 cm water applied for 80–60 minutes. The Southern blot was then baked at 80° C. for 2 hours and stored in a vegetable freezing bag.

Southern hybridization

The Southern blot was placed in a heat sealable plastic bag and incubated with 10 ml of pre-hybridization buffer containing 1M NaCl, 1% SDS, 10% dextran sulphate, and 200 μg/ml herring sperm DNA, and incubated for 15 minutes at 65° C. A corner of the bag was then cut off, and the radiolabelled oligonucleotide probe was added (approximately $10^7$ dpm). The bag was resealed and placed at 65° C. in an oven or waterbath and gently rocked or shaken for 12–16 hours. The membrane was then removed from the bag and washed in a series of increasingly dilute and higher temperature (increasing stringency) SSC buffers until the background radioactivity was low relative to the specifically bound probe. In a dark-room, the membrane was then placed in a plastic bag which was positioned in an X-ray film cassette equipped with intensifier screens, a sheet of Kodak XAR-5 film was added, and the sealed cassette was placed at −70° C. for variable time depending on the intensity of signal. Usually, exposures after varying time periods are useful. The film was developed in a Kodak X-OMAT automatic developer. Membranes may be re-hybridized several times. Nytran membranes may be stripped of labeled probe by heating in boiling 0.1×SSC for 2 minutes.

Northern analysis

Total RNA was prepared as described herein above. The RNA was electrophoresed in an agarose gel. The gel (1–1.2% agarose) was prepared in MOPS buffer containing 2% formaldehyde and 10 μg/ml ethidium bromide and poured into a plastic mold for horizontal electrophoresis. Fifteen to twenty μg of RNA in a loading buffer containing 10% formaldehyde, 72% formamide, 8% glycerol, and bromphenol blue was denatured by heating at 95° C. for 2 minutes, loaded into wells of the agarose gel and electrophoresed at 200 volts for 2–3 hours. One well was loaded with bacterial ribosomal RNA markers. Following electrophoresis, the gel was photographed on a UV transilluminator with a rule in place to record the positions of human 28S and 18S RNA (5.1 and 2.0 kb respectively) and bacterial 23S and 16S RNA (2.9 and 1.6 kb respectively). The gel was then rinsed and vacuum transferred in 10×SSC to a Nytran membrane, as described above. The Northern blot was hybridized to radiolabelled probe vide supra.

Karyotype and Isozyme Analysis

These studies were conducted by the method of Peterson et al in: Methods in Enzymology: Cell Culture. Academic Press, 58: 164–178, 1979.

DNA Fingerprint Analysis

These studies were performed essentially as described by Jeffreys et al (*Nature* 314, 316). Purified DNA (10–20 μg) was digested with restriction endonuclease Hinf I (New England Biolabs, Beverly, Mass.). The sample was then divided in two. The resulting fragments of DNA in both samples were size fractionated by agarose gel electrophoresis on separate gels. The DNA fragments were transferred by Southern blotting to nylon membranes (Hybond, Amersham, Arlington Heights, Ill.). DNA probes were prepared from the human multi-locus probes 33.6 and 33.15, or a combination of four single locus probes (MS1, MS31, MS43, and G3) and were labelled with 32P-dGTP (New England Nuclear/DuPont, Boston, Mass.) using a modification of the method of Feinberg and Vogelstein (Analytical Biochemistry Vol. 132, 1983 pp. 6–13). Hybridization conditions were a modification of the method of Jeffreys, et al (*Nature* 314, 316). DNA band patterns were visualized following autoradiography (Lightning Screens, DuPont, Boston, Mass.). The samples evaluated were DNA from different passages of the three cell lines BEP1, 2, and 3, and DNA from the putative donor, and 6 controls.

The availability of three unique immortalized human bronchial epithelial cell lines of the present invention transformed by two different strains of human papilloma virus now makes it possible for the first time to determine various factors and parameters controlling not only the expression of HPV genes but also the behavior, proliferation, differentiation of neoplastic human bronchial epithelial cells (HBE) as well as the identification of chemical and biological agents that may be useful in the therapy of human lung cancer. This is achieved by standard protocols comparing normal and transformed HBE cells for growth and inhibition requirements, transcription and translation controlling factors, suppressor elements, cellular enhancer and regulatory proteins, DNA repair, altered metabolism, response to metals, tobacco components, biological and chemical agents and the like.

A deposit of two immortalized NHBE cell lines, designated herein BEP1 and BEP2 has been made at the ATCC, Rockville, Md. on Feb. 21, 1990 under accession numbers CRL10360 and CRL10361, respectively, representing transformation by HPV-18. A deposit of the third immortalized NHBE cell line transformed by HPV-16 and designated herein BEP3 has been made at the ATCC, Rockville, Md., on Mar. 2, 1990 under accession number CRL10365. The deposits shall be viably maintained, replacing If a deposit becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the The Commissioner of Patents and Trademarks, upon law request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An immortalized human bronchial epithelial cell line containing actively expressing HPV16 or HPV18 genes.

2. A method for determining the factors controlling growth, inhibition and neoplastic transformation of human bronchial epithelial cells, comprising the step of comparing the behavior of normal bronchial epithelial cells with immortalized cell line of claim 1 in the presence of a factor whose effect on the growth, inhibition, neoplastic transformation or differentiation is to be determined.

3. An immortalized human bronchial epithelial cell line actively expressing HPV16 genes.

4. The cell line of claim 3 being ATCC deposit CRL 10365.

5. An immortalized human bronchial epithelial cell line actively expressing HPV18 genes.

6. The cell line of claim 5 selected from the group consisting of ATCC deposits CRL 10360 and 10361.

7. The cell line of claim 6 being ATCC deposit CRL 10360.

8. The cell line of claim 6 being ATCC deposit CRL 10361.

* * * * *